US007618584B2

(12) United States Patent
Lampeter et al.

(10) Patent No.: US 7,618,584 B2
(45) Date of Patent: Nov. 17, 2009

(54) BAG SYSTEM FOR THE CRYOPRESERVATION OF BODY FLUIDS

(75) Inventors: Eberhard Lampeter, Leipzig (DE); Dietmar Egger, Mössingen (DE)

(73) Assignee: Vita 34 AG, Leipzig (DE)

( * ) Notice: Subject to any disclaimer, the term of this patent is extended or adjusted under 35 U.S.C. 154(b) by 321 days.

(21) Appl. No.: 10/473,094

(22) PCT Filed: Oct. 16, 2002

(86) PCT No.: PCT/EP02/11564

§ 371 (c)(1),
(2), (4) Date: Sep. 25, 2003

(87) PCT Pub. No.: WO03/041634

PCT Pub. Date: May 22, 2003

(65) Prior Publication Data

US 2004/0097862 A1    May 20, 2004

(30) Foreign Application Priority Data

Oct. 22, 2001  (DE)  .............................. 101 51 343

(51) Int. Cl.
*A61B 19/00* (2006.01)
(52) U.S. Cl. .......................... 422/45; 604/410; 604/408; 604/403
(58) Field of Classification Search ................ 604/6.15, 604/6.16, 403, 408, 410; 220/501; 383/210, 383/42, 38; 435/2, 284.1, 325, 372, 374; 600/573, 580
See application file for complete search history.

(56) References Cited

U.S. PATENT DOCUMENTS

| 4,775,360 A | * | 10/1988 | Lane et al. ................. 604/6.09 |
| 5,092,996 A | * | 3/1992 | Spielberg ..................... 604/410 |
| 5,217,617 A | * | 6/1993 | Duncan et al. .............. 210/620 |
| 5,217,627 A | * | 6/1993 | Pall et al. .................... 210/767 |
| 5,356,373 A | | 10/1994 | Dracker |

(Continued)

FOREIGN PATENT DOCUMENTS

EP            0 542 221 A1    5/1993

*Primary Examiner*—Leslie R Deak
(74) *Attorney, Agent, or Firm*—Evelyn H. McConathy; Montgomery, McCracken, Walker & Rhoads, LLP

(57) ABSTRACT

The invention relates to a bag system for the cryopreservation of body fluids, that is blood, bone marrow or umbilical cord blood, the parts of the bag system being sterilized, and separable from one another, wherein liquids which permit and/or assist cryopreservation are located in the bag system and/or may be introduced into the bag system in a sterile form. The bag system, at least, comprising: a device for the direct removal of body fluid (1) from the living body, a region or number of regions for mixing the liquids with the body fluid and/or for storing the mixture of liquids and body fluid, a number of shut-off elements (2) and connecting lines (3) and an inlet element (4) and/or an outlet element (5). The bag system is characterized in that the parts of the bag system, which are connected in a communicating manner to one another by the connecting lines (3), form a closed, sterile system before the bag system is used, and the regions for storing the mixture of liquids and the body fluid are hermetically sealable and separable from one another.

24 Claims, 9 Drawing Sheets

U.S. PATENT DOCUMENTS

| | | | |
|---|---|---|---|
| RE35,804 E | * | 5/1998 | Stewart ...................... 210/767 |
| 5,879,318 A | | 3/1999 | Van Der Heiden et al. |
| 5,928,214 A | * | 7/1999 | Rubinstein et al. .......... 604/410 |
| 6,059,968 A | | 5/2000 | Wolf, Jr. |
| 6,232,115 B1 | | 5/2001 | Coelho et al. |
| 6,267,745 B1 | * | 7/2001 | Mathias et al. ............. 604/4.01 |
| 6,267,925 B1 | * | 7/2001 | Pages ......................... 422/41 |
| 6,328,726 B1 | * | 12/2001 | Ishida et al. ................ 604/408 |
| 6,491,678 B1 | * | 12/2002 | Rubinstein et al. .......... 604/410 |
| 2005/0084838 A1 | * | 4/2005 | Lampeter .................... 435/1.3 |

* cited by examiner

BAG SYSTEM FOR THE CRYOPRESERVATION OF BODY FLUIDS

BACKGROUND OF THE INVENTION

Field of the Invention

The invention relates to a bag system for the cryopreservation of body fluids, that is blood, bone marrow or umbilical cord blood, the parts of the bag system being sterilized and separable from one another and liquids which permit and/or assist cryopreservation being located in the bag system and/or able to be introduced into the bag system in a sterile form, at least comprising: a device for the direct removal of body fluid from the living body, a region or number of regions for mixing the liquids with the body fluid and/or for storing the mixture of liquids and body fluid (fluid store), a number of shut-off elements and connecting lines and an inlet element and/or an outlet element. A further aspect of the invention relates to a method of preparing body fluids, that is blood, bone marrow or umbilical cord blood, for long-term storage by cryopreservation in a transporting and storing system, at least comprising the steps of: introducing the body fluid into the transporting and storing system, providing or adding liquids which permit and/or assist the cryopreservation, and transferring the mixture of liquids which permit and/or assist the cryopreservation and the body fluid into a region for storage in the transporting and storing system.

The cryopreservation of body fluids, that is blood, bone marrow or umbilical cord blood, has assumed immense commercial significance as the constant development in human medicine has progressed.

Umbilical cord blood and its preservation over a number of years, known as long-term preservation, are crucially significant in connection with possible later treatment of the child, youngster or adult with means based on the body's own substances, for example in the situation of a transplant. This is because this valuable blood is available only at the birth of the child. After the umbilical cord has been cut, it still contains blood which is not required for the child. In the case in which long-term preservation is intended, this blood, often an amount of blood with a volume of about 50 to 100 ml, is taken up and prepared for cryopreservation and subsequently frozen by known methods. The aforementioned small amounts of blood removed must expediently be frozen and stored in such a way that a number of samples can be examined and used independently and at different times from one another, possibly several years apart, by the latest methods then available. Without knowledge today of the methods which will be applied then, cryopreservation of all constituents of the body fluid removed is considered appropriate.

At present, separate systems are used for the preparation and freezing. For instance, the umbilical cord blood is taken up by a system which often comprises one or more removal cannulas, one or two containers which contain citrate, and the actual blood collecting container, the aforementioned parts of the system being connected in a communicating manner to one another by flexible tubes. Such a system is known as prior art, for example from U.S. Pat. No. 5,879,318.

Following the preparation of the blood, decanting then takes place from one system into another for the purpose of cryopreservation, that is from a sterile container into a sterile freezing container, which often has to be performed under ultraclean room conditions. Assurance of the statutory predetermined ultraclean room conditions with respect to human medicine, for example the requirements according to GMP, often requires high investment expenditure, which usually cannot be provided in every delivery ward or medical facility removing the body fluids in sterile form and preparing them for cryopreservation.

Until now, the preparation for cryopreservation of umbilical cord blood always took place by the following steps:

Removal of the blood and introduction into the transporting bag. Addition of citrate, unless already provided, closing of the bag and transport at room temperature to an ultraclean room within about 24 to 48 hours. Transfer of the blood and added cryoprotectant from the transporting bag into a sterile freezing bag under ultraclean room conditions, at least two separate systems have always been used.

SUMMARY of THE INVENTION

An object of the invention is to provide a bag system which reduces the costs of preparing for and carrying out cryopreservation and allows easy and safe manual handling, while having to ensure that the requirements for sterility in human medicine are met. Furthermore, it is an object of the invention to provide a method of preparing body fluids, that is blood, bone marrow and umbilical cord blood, for long-term storage by cryopreservation which uses a transporting and storing system of the aforementioned type.

The object of the invention is achieved by the parts of the bag system which are connected in a communicating manner to one another by the connecting lines forming a closed, sterile system before the bag system is used and the regions for storing the mixture of liquids and the body fluid being hermetically sealable and separable from one another.

The invention makes it possible to provide a bag system which forms what is known as a closed system, at least at the time at which the body fluid is introduced, in particular directly from the human body. Consequently, optimum sterility is achieved and there is the possibility of separating parts of the bag system which are no longer required, in particular in connection with the actual cryopreservation, step by step from the bag system.

The parts which are no longer required for expedient handling, such as for example the device for taking up the body fluid after transferring the body fluid into a region for mixing, are separated from the bag system. At the time of freezing, the closed system then only comprises parts which are separated and hermetically sealed from one another and are no longer connected in a communicating manner to one another. Savings with respect to transporting and storage costs are thereby achieved.

The feature according to the invention that the regions for storing the mixture of liquids which permit and/or assist the cryopreservation and the transferred body fluid are hermetically sealable and separable from one another makes it possible to separate the total amount of the aforementioned mixture into a number of part-amounts which are separate from one another and desired with respect to the size of their volume. These separated part-amounts are available in particular after freezing for bacteriological and serological examinations and for monitoring the long-term storage, without opening the complete bag system. The entire handling in the laboratory, for example the adding of a cryoprotectant via a sterile filter, can be performed under normal hygienic conditions (for example clean room class D); ultraclean room conditions are not required.

The materials used for the parts of the bag system are selected and adapted to one another in a known manner, in particular in respect of the function of the respective part, the type of the medium or media with which it comes into contact, the acting time of the medium, the type and manner of the sterilization and the temperature regime, i.e. in particular the maximum and minimum temperature to be encountered during handling and freezing. Known plastics which meet the aforementioned requirements and are authorized for applications in human medicine are mainly used for this.

Liquids which permit and/or assist the cryopreservation are, for the purposes of the invention, media known in this respect. For the cryopreservation of blood, they are, for example, liquid media for the prevention of blood coagulation, such as citrate phosphate dextrose (CPD), for the thinning of the blood, such as sodium chloride solutions, and cryoprotectants, such as DMSO.

Regions for mixing the liquids with the body fluid and/or for storage are, for the purposes of the invention, all known closable liquid stores, such as for example containers and bags of medical and laboratory technology which are formed in such a way as to be liquid-tight with respect to the atmosphere.

In a preferred configuration according to the invention, the regions for storing the mixture of liquids and the body fluid are configured in such a way. that they are at least two chambers of a bag. Two chambers permit the separation of two part-amounts of the liquid mixture to be stored, so that a subdivision which is also expedient for practical purposes with respect to the complete amount of liquid is possible. The use of a bag which has flexible walls is particularly advantageous if the handling is carried out manually by midwives or medical personnel. Exposure of the flexible walls to manual pressure and the use of gravity have the effect of transporting the liquid and gas within the bag system and of bringing about thorough internal mixing.

A further advantageous configuration is that a region for storing the mixture of liquids and the body fluid is a connecting line, which preferably has a number of segments which can be hermetically sealed and separated from one another. This configuration achieves the effect that smaller part-amounts, which serve in particular as samples for monitoring long-term preservation, are separated in a simple manner, for example by hermetic sealing by means of welding the flexible and transparent connecting line which is arranged between the freezing bag and the mixing bag or between the freezing bag and the sterile filter used for venting.

It is also advantageous that a filling level indication is arranged at least in the respective region for mixing the liquids. The filling level indication may take place by applying corresponding markings on the wall of the transparent bag, so that in particular the minimum filling height for the body fluid introduced and the set filling height, which is to be achieved after filling with the thinning liquid, can be monitored.

In connection with long-term preservation, it is also advantageous that the regions for storing the mixture of liquids and the body fluid which have been separated from the other parts of the system can be surrounded by an enclosure 8. This enclosure serves in particular for mechanical protection and may additionally ensure gas-tight and liquid-tight enclosure.

It is particularly advantageous that, in particular with regard to its dimensioning and material selection, the bag system is intended for being used once. Disposable systems or their parts have a range of known advantages, knowledge that they will be used only once, possibly used only briefly, such as for example the device for removing the body fluid, permitting inexpensive manufacture of the part or system.

For certain applications it is advantageous that the region for mixing the liquids with the body fluid and the region for storing the mixture of liquids and body fluid are arranged in a mixing and freezing bag 16, the mixing and freezing bag 16 having a mixing and freezing chamber 9 or a mixing and freezing chamber 9 and a freezing chamber 10.

Fewer parts of the bag system are less expensive and permit easier handling. This is the case for example whenever it is ensured that freezing begins within a relatively short time, i.e. within 10 to 20 minutes, after the body fluid has been taken up into the bag system.

Alternatively, the following configuration of the bag system according to the invention is preferred, that is that the region for mixing the liquids with the body fluid is arranged in a mixing bag 11 and the region for storing the mixture of liquids and body fluid is arranged in a freezing bag 12, this bag having a freezing chamber 9 or two freezing chambers 9.

The use of a number of bags, that is one for mixing and one for storing, which may consist of different materials, brings about better handling and consequently enhanced functional dependability by eliminating subjective manipulation errors. For example, specific material selection makes it possible in the case of a bag system for umbilical cord blood to provide CPD in a mixing bag already while the complete bag system is being assembled, so that there is no longer any need for otherwise sterile filling of CPD into the bag system immediately before the umbilical cord blood is taken up in the delivery room. It is also consequently possible that the freezing must be performed only within about 20 hours after the take-up of the blood into the bag system if significant damage to constituents of the blood is not to occur, allowing intermediate storage at room temperature before freezing. The selection of the material for this freezing bag 12 is primarily determined by its temperature resistance with respect to the actual cryopreservation (temperatures down to about −196° C.); sterilization by autoclaving is consequently often ruled out.

For the aforementioned form of the bag system with two bags for mixing and storing, it is further preferred that the mixing bag 11 and the freezing bag 12 are connected to each other by two connecting lines. Blood or umbilical cord blood has a tendency to foam, in particular during mixing with other liquids, i.e. air bubbles are trapped in the liquid or in the liquid mixture, with the result that a liquid-air mixture is obtained. With this type of arrangement, i.e. a closed circuit between the two bags, the liquid-air mixture contained in the bag system can be manipulated in such a way that there are no or few inclusions of air in the liquid at the time of freezing in the amount of liquid which is located in the region or the regions for storing.

Alternatively, it is advantageous that the mixing bag 11 and the freezing bag 12 are connected to each other by a connecting line. This configuration expediently requires the arrangement of an outlet element on the freezing bag, for example a sterile filter, which serves in particular for the discharge of air from the bag system.

The object of the invention is also achieved by a method in which the parts of a transporting and storing system which are connected in a liquid-communicating manner to one another form a closed, sterile system before the body fluid is introduced into the transporting and storing system, and the region or the regions for storing the mixture of liquids and the body fluid are hermetically sealable and separable from one another.

The method according to the invention may alternatively be used for human body fluids: blood, bone marrow or umbilical cord blood. Use of the method is also suitable in principle for other human or animal body fluids.

Use of the method according to the invention is particularly advantageous in the case where the transporting and storing system is a bag system according to claims 1 to 11. In principle, the method can also be applied if, instead of bags, the transporting and storing system uses other known liquid stores of medical and laboratory technology, such as bottles or containers. In this case, it is expedient to use customary means, such as pumps, at least for part of the liquid communication in the transporting and storing container.

It is particularly economical in terms of the method that a defined amount of the mixture of liquids which permit and/or assist the cryopreservation and the body fluid is transferred into a region for storage. The transferring and storing of a specific amount of liquid, for example 160 ml, permits easy and consequently low-cost freezing with conventional equipment for cryopreservation.

It is also preferred that the mixture of liquids which permit and/or assist the cryopreservation and the body fluid is transferred virtually without any bubbles into a region for storing. Freedom from bubbles is an important criterion for the quality and, consequently, the suitability for the intended use of the liquid mixture to be stored. This requires for example the arrangement of an outlet element and/or of the corresponding connecting lines, so that manual manipulation can be performed until the liquid mixture is virtually free from bubbles.

The invention is to be explained in more detail below on the basis of an exemplary embodiment of a bag system for umbilical cord blood. In the drawing:

DESCRIPTION OF THE PREFERRED EMBODIMENTS

Figure 1:
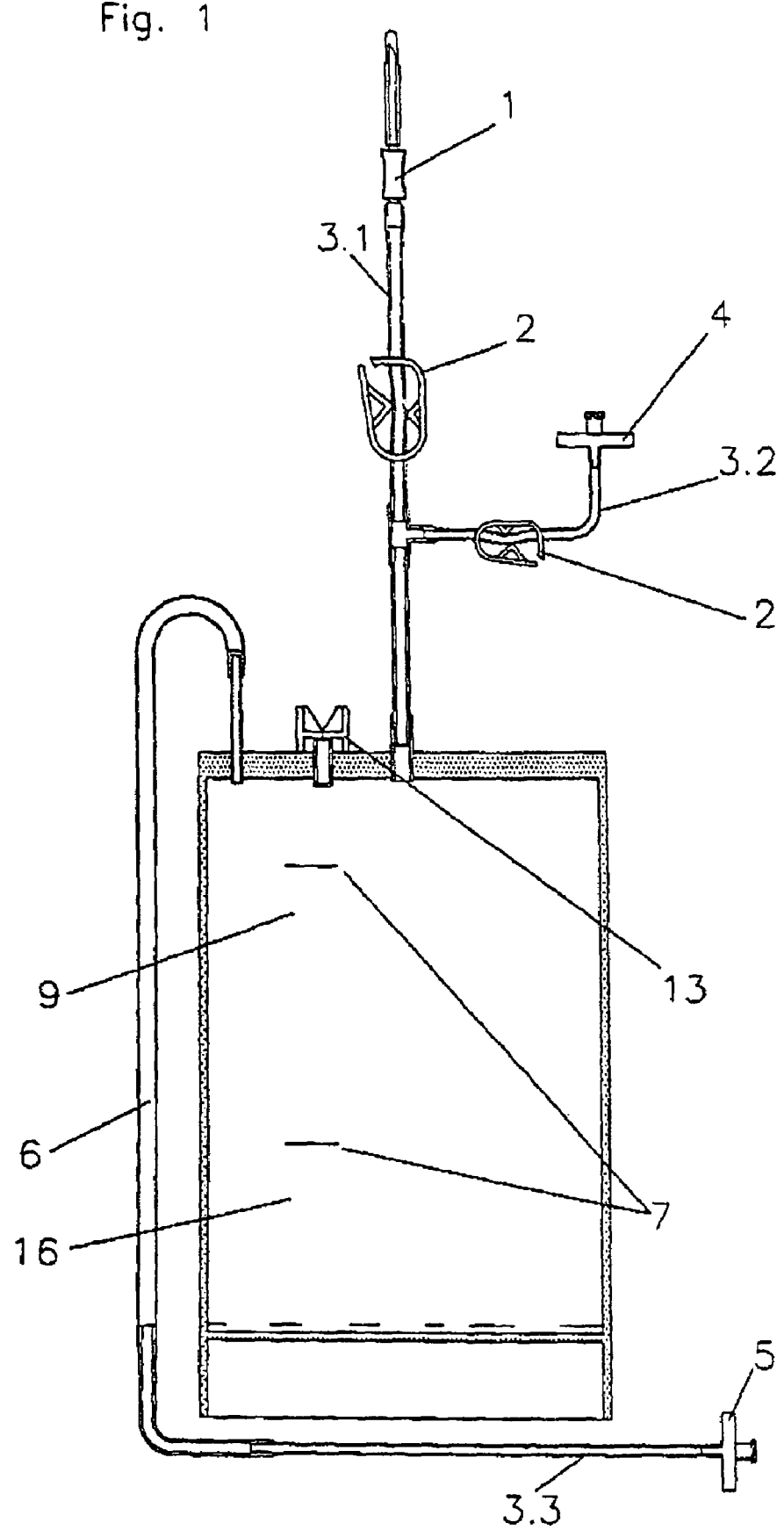
FIG. 1 shows a bag system with a mixing and freezing bag.

FIG. 1 shows a bag system with a mixing and freezing bag 16, which is connected in a communicating manner by three connecting lines 3.1, 3.2 and 3.3 to a device for the direct removal of umbilical cord blood 1, an inlet element 4 and an outlet element 5. The communication, i.e. in particular the liquid transport and the air exchange, between the aforementioned parts of the bag system is realized by opening or closing of the shutoff elements 2, which take the form of commercially available hose clips. The transport of the liquid media, possibly with air inclusions, is realized in the bag system by using gravity and by exertion of manual pressure on the flexible walls of the bags. The inlet element 4, which in this configuration is a sterile filter, serves for the sterile introduction of the liquids which permit and/or assist cryopreservation, i.e. in particular a liquid for avoiding blood coagulation (A), a liquid for thinning (B) and/or a liquid cryoprotectant (C).

After the introduction of the umbilical cord blood and/or liquids which permit and/or assist cryopreservation, the connecting lines 3.1 and 3.2, which consist of a plasticized PVC material, can be hermetically sealed and/or separated by welding, for example with a transportable film welding appliance. Like the connecting lines 3, the flexible mixing and freezing bag 16 substantially consists of an EVA plastics material, ethylene vinyl acetate, which is temperature-resistant at least down to a temperature of −196° C. and can be sterilized by radiation sterilization (gamma radiation). On the transparent freezing bag 16, which is designed for a maximum volume of 180 ml, there is a filling level indication 7, which indicates the values for the minimum filling amount of 60 ml and the set filling amount of 160 ml. Arranged on the mixing and freezing bag 16 is a removal adaptor 13, which permits the sterile removal of the stored liquid mixture. The connecting line 3.3 is connected to an outlet element 5, which is a sterile filter and serves in particular for the air discharge from the bag system. The thin-walled, flexible and transparent connecting line 3.3 is a region for storing the mixture of liquids and the body fluid. These segments 6, for example five of them, with a capacity of in each case about 1 ml, which are hermetically sealable and separable from one another, not represented in FIG. 1, can be produced by welding, for example with a transportable film welding appliance, from part of the connecting line 3.3. The joining together of the previously sterilized parts of the bag system, which comprise commercially available parts and components, to form a closed system for the purposes of the invention is performed under ultraclean room conditions. Welding, adhesive bonding and joining techniques authorized for human medicine can be used for the joining together.

Figure 2:
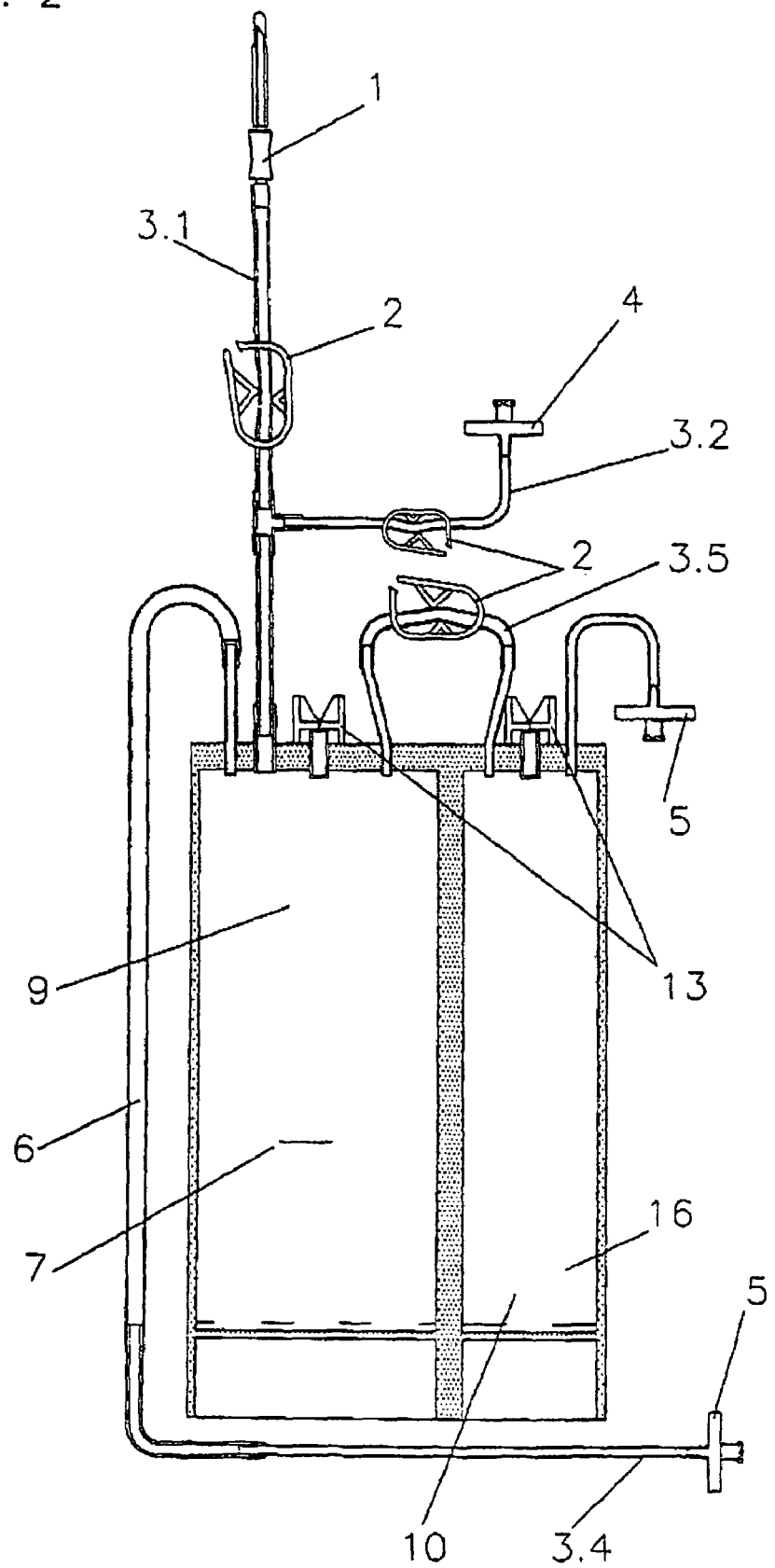
FIG. 2 shows a bag system with a mixing and freezing bag which has a mixing and freezing chamber and a freezing chamber.

The bag system represented in FIG. 2 shows a mixing and freezing bag 16, which has a mixing and freezing chamber 9 and a freezing chamber 10, which are connected in a communicating manner to each other. The mixing and freezing bag 16 communicates via a number of connecting lines 3 with a device for the direct removal of umbilical cord blood 1, an inlet element 4 and two outlet elements 5. The two chambers, which can be separated from each other, that is the mixing and freezing chamber 9 and the freezing chamber 10, in each case have a removal adaptor 13 and an outlet element 5.

Figure 3:
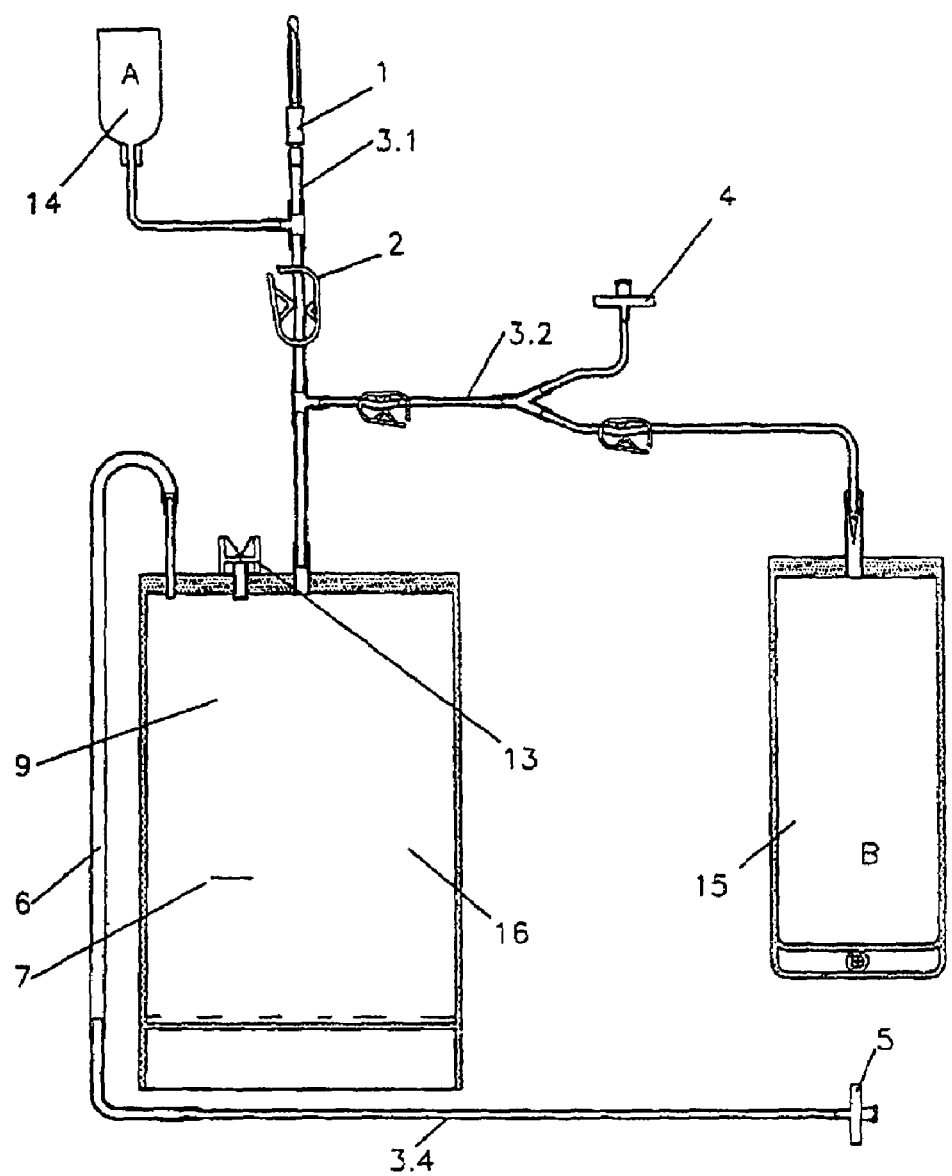
FIG. 3 shows a bag system with a mixing and freezing bag which has a mixing and freezing chamber and a sodium chloride bag.

The configuration presented in FIG. 3 differs from FIG. 1 in that a bag 14, which contains 21 ml of CPD, a liquid for avoiding blood coagulation (A), and a bag 15, which contains 100 ml of a sodium chloride solution (NaCl), which are respectively connected to the closed bag system via a connecting line 3, are arranged. The bags 14 and 15 have in each case an interruption valve with respect to the connecting line 3.

Figure 4:
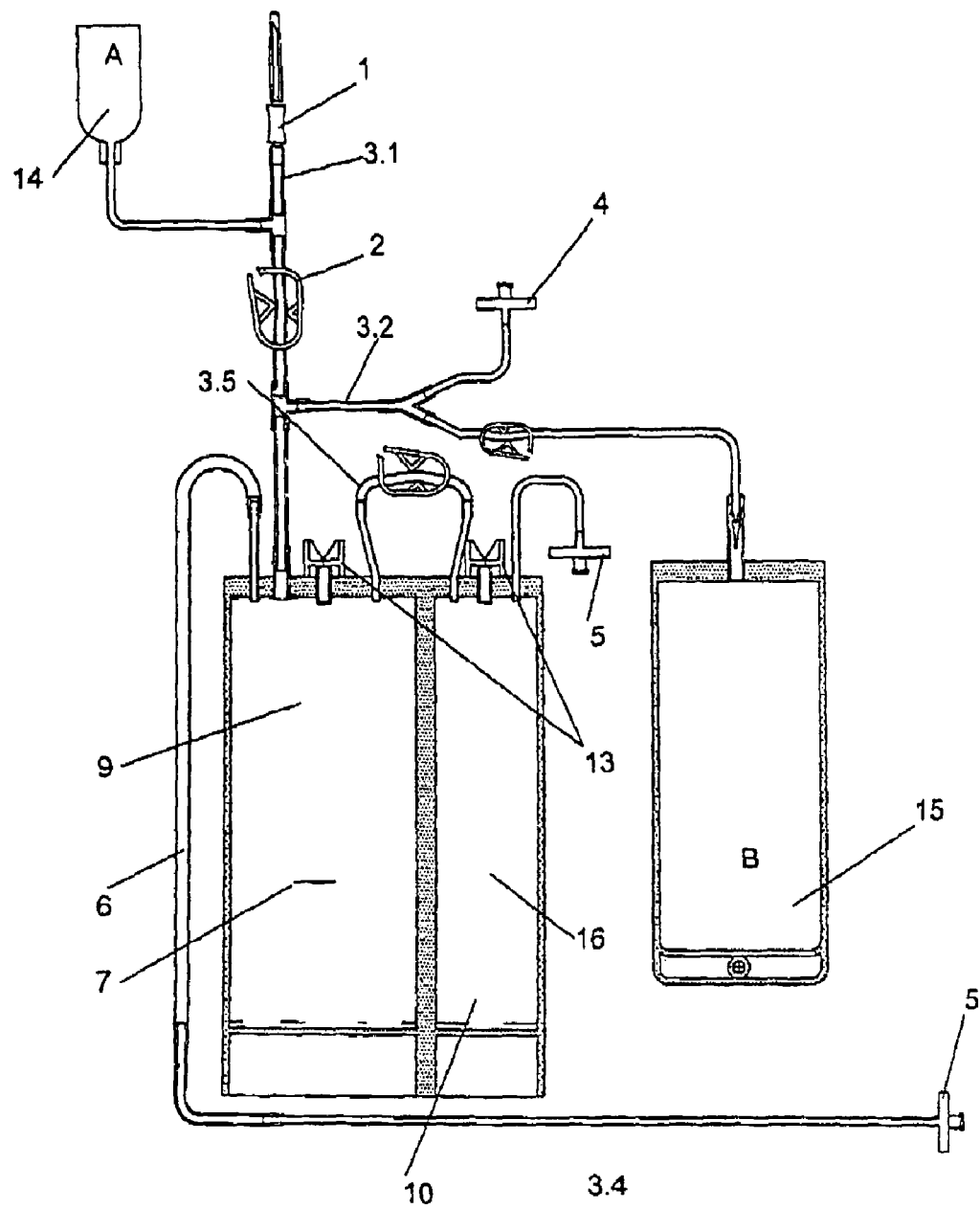
FIG. 4 shows a bag system with a mixing and freezing bag which has a bag for a liquid for avoiding blood coagulation and a sodium chloride bag.

In FIG. 4, the bag system has a mixing and freezing bag 16, which as a difference from FIG. 3 contains two chambers, that is a mixing and freezing chamber 9 and a freezing chamber 10.

Figure 5:
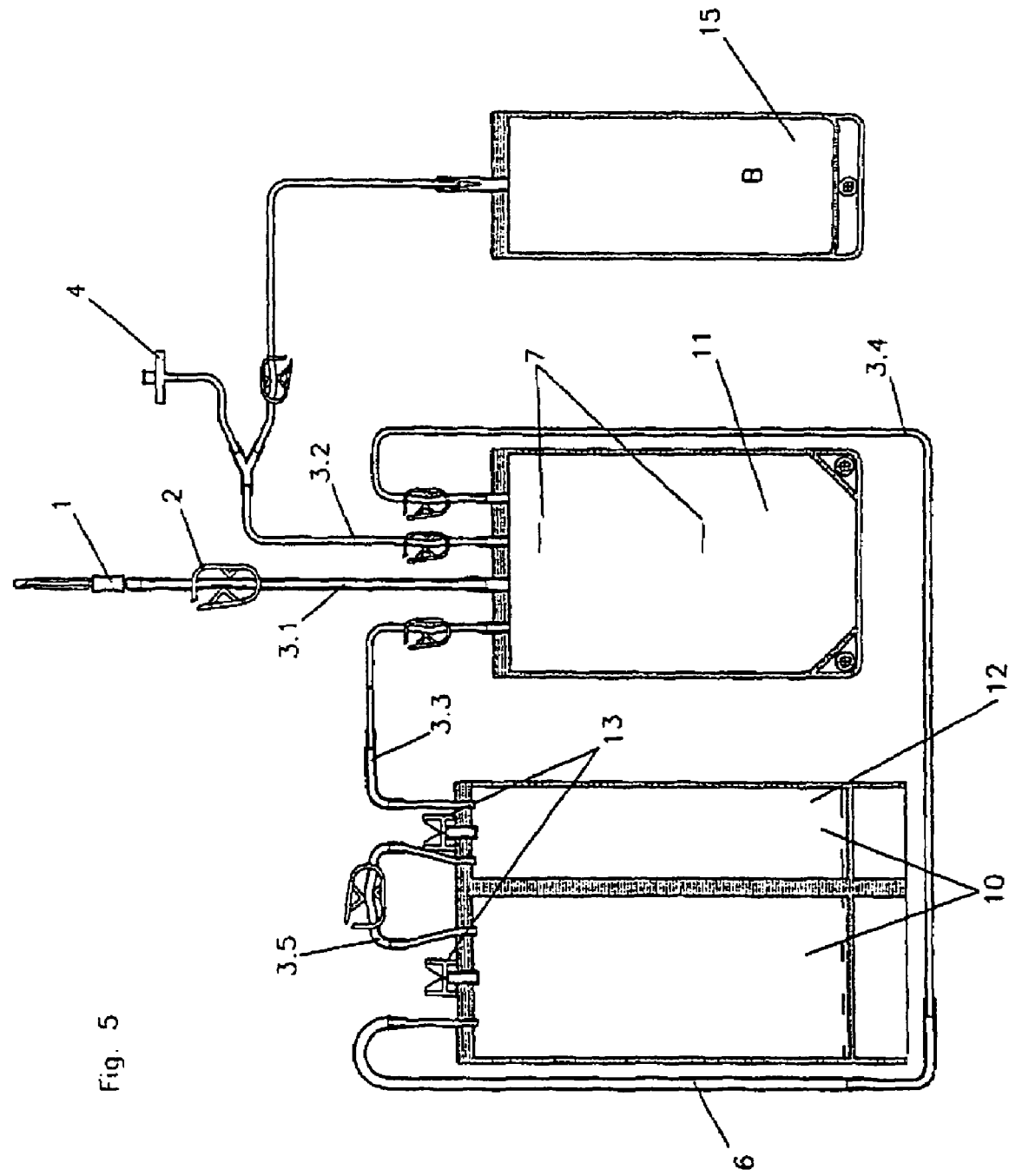
FIG. 5 shows a bag system which has a freezing bag with two chambers and a mixing bag and two connecting lines between the freezing bag and the mixing bag.

Represented in FIG. 5 is a bag system comprising a mixing bag 11, which is connected in a communicating manner by four connecting lines 3.1, 3.2, 3.3 and 3.4 to a device for the direct removal of umbilical cord blood 1, an inlet element 4, a freezing bag 12 and a bag 15. The communication, i.e., in particular the liquid transport and the air exchange, between the aforementioned parts of the bag system is realized by opening or closing the shut-off elements 2. The liquid media, possibly with air inclusions, are mixed, moved and transported in the bag system by using gravity and by exertion of manual pressure on the flexible walls of the bags. The inlet element 4, which in this configuration is a sterile filter, serves for the sterile introduction of a liquid cryoprotectant C, for example DMSO. After the introduction of the umbilical cord blood and/or liquids which permit and/or assist cryopreservation, the connecting lines 3.1 and 3.2 can be hermetically sealed and/or separated by welding. CPD may be provided in the mixing bag 11. Like the connecting lines 3, the flexible mixing bag 11 substantially consists of a plasticized PVC plastics material, which can be sterilized in a way known, e.g. by autoclaving. On the transparent mixing bag 11, which is designed for a maximum volume of 180 ml, there is a filling level indication 7, which indicates the values for the minimum filling amount of 60 ml and the set filling amount of 160 ml. Arranged on the freezing bag 12, which substantially consists of an EVA plastics material and has two freezing chambers 10, at each freezing container 10 is a removal adaptor 13, which permits the sterile removal of the stored liquid mixture. The connecting lines 3.3 and 3.4 connect the mixing bag 11 and the freezing bag 12 to each other. One of the thin-walled, flexible and transparent connecting lines 3.3 or 3.4 may be a region for storing the mixture of liquids and the body fluid. These segments 6, for example five of them, with a capacity of in each case about 1 ml, which are hermetically sealable and separable from one another, not represented in FIG. 5, can be produced by welding, for example with a transparent film welding appliance, from part of the connecting line 3.3 or 3.4. The two freezing chambers 10 are connected to each other in a communicating manner by a connecting line 3.5. After the hermetic sealing and separating of the connecting lines 3.3, 3.4 and 3.5 from the mixing bag 11 and freezing bag 12, the two freezing chambers 10 are separable from each other.

The joining together of the previously sterilized parts of the bag system, which comprise commercially available parts and components, to form a closed system for the purposes of the invention is performed under ultraclean room conditions. Welding, adhesive bonding and joining techniques authorized for human medicine can be used for the joining together.

Figure 6:
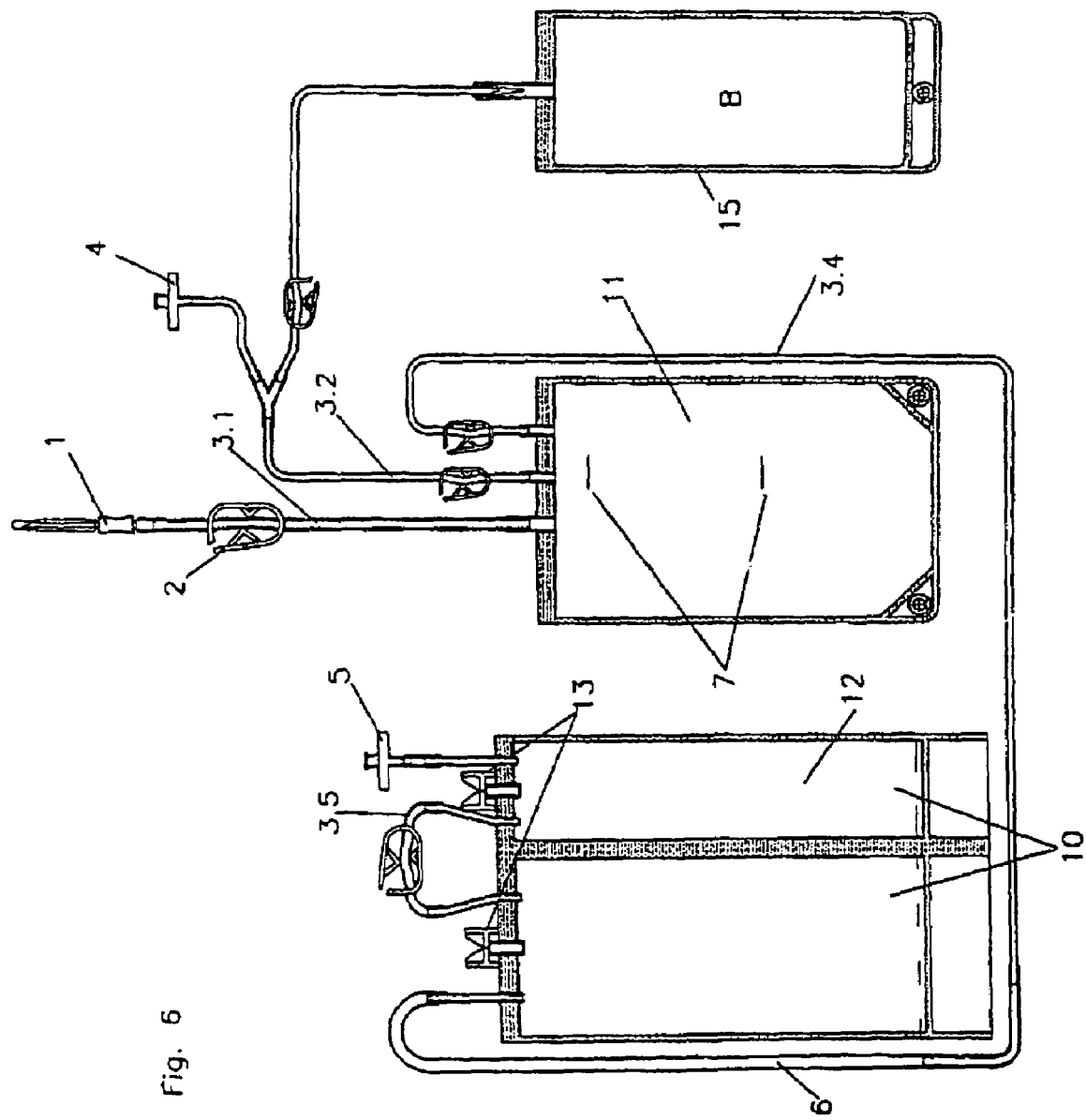
FIG. 6 shows a bag system which has a freezing bag with two chambers and a mixing bag and a connecting line between the freezing bag and the mixing bag.

FIG. 6 shows a bag system analogous to FIG. 5, the mixing bag 11 and the freezing bag 12 being connected by a connecting line 3.4. The absent connecting line 3.3 is substituted by an outlet element 5, which is a sterile filter, which serves in particular for venting.

Figure 7:
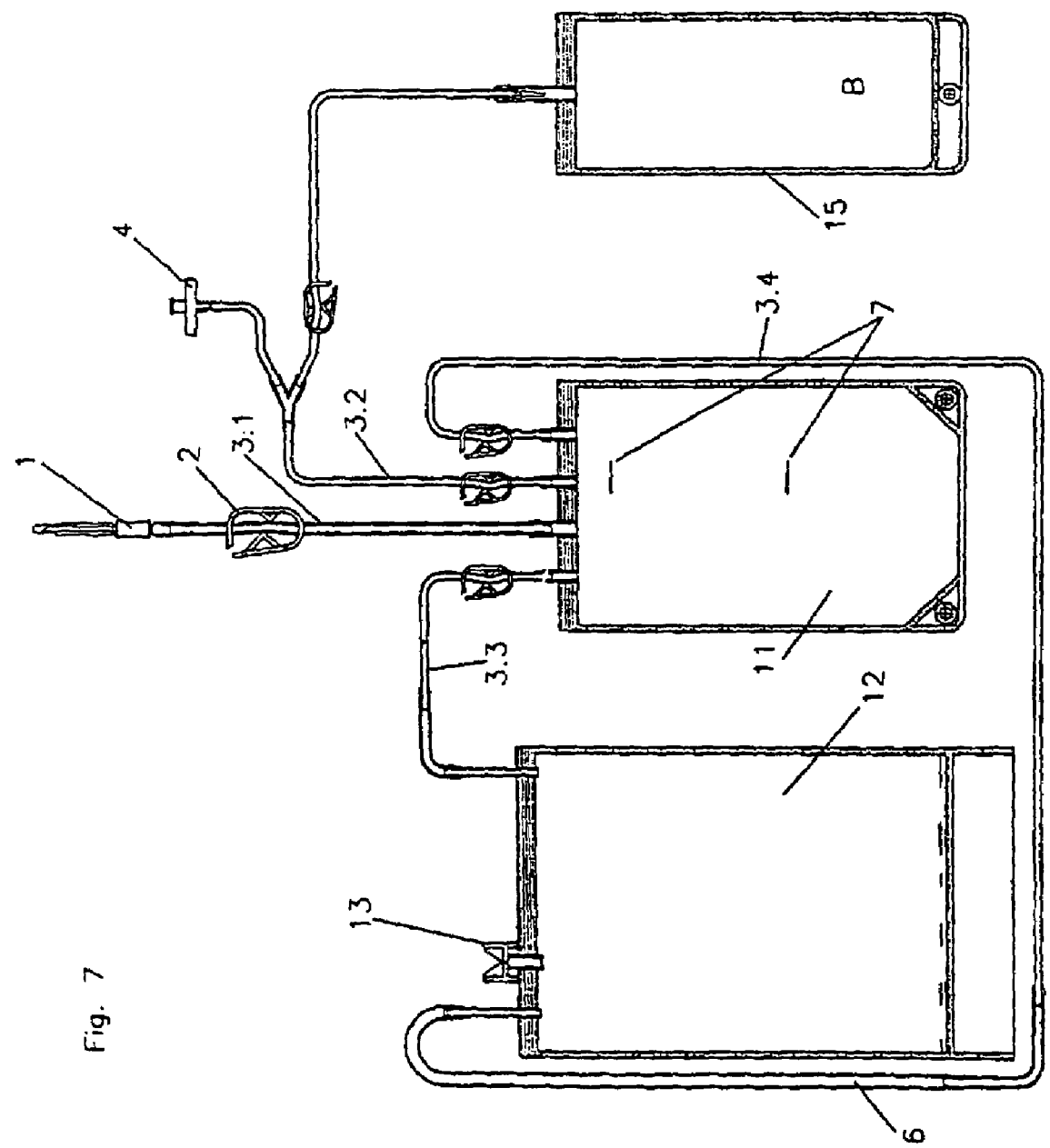
FIG. 7 shows a bag system which has a freezing bag with a chamber, a mixing bag and two connecting lines between the freezing bag and the mixing bag.

In FIG. 7 the bag system is represented analogously to FIG. 5, the freezing bag only having one freezing chamber 10.

Figure 8:
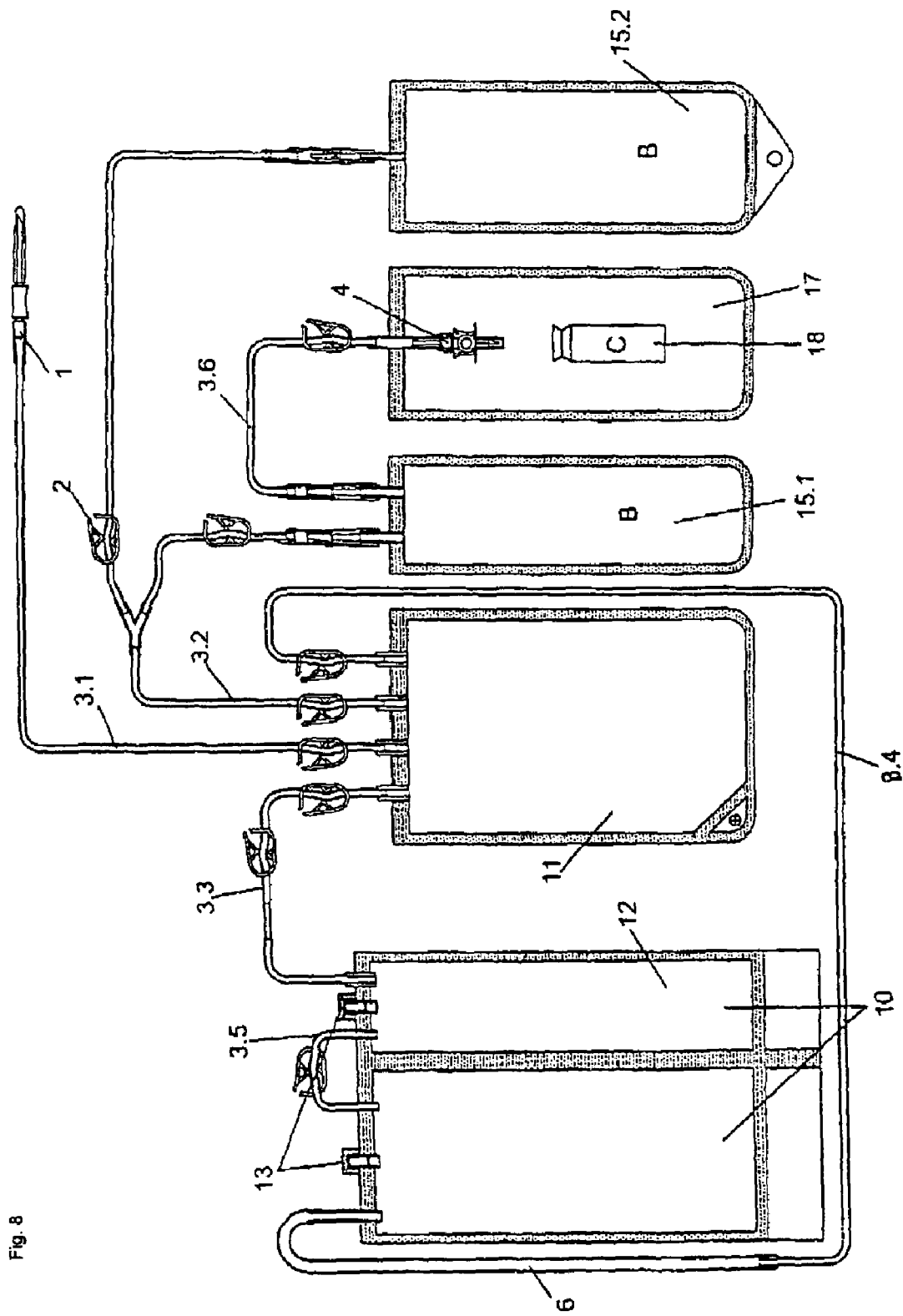
FIG. 8 shows a bag system with a glass ampoule in the protective bag and FIG. 9 shows parts of a bag system before freezing.

Represented in FIG. 8 is a bag system comprising a mixing bag 11, which is connected in a communicating manner by four connecting lines 3.1, 3.2, 3.3 and 3.4 to a device for the direct removal of umbilical cord blood 1, a freezing bag 12 and two bags 15.1 and 15.2. The communication, i.e., in particular the liquid transport and the air exchange, between the aforementioned parts of the bag system is realized by opening or closing the shut-off elements 2. The liquid media, possibly with air inclusions, are transported in the bag system by using gravity and by exertion of manual pressure on the flexible walls of the bags. The inlet element 4, which in this configuration is a tapping pin for a pierceable stopper of a glass ampoule 18, serves for the sterile introduction of a liquid cryoprotectant C, for example, 10 ml of DMSO. The glass ampoule 18 is arranged in a hermetically sealed protective bag 17, which is connected to the bag 15.1 via a connecting line 3.6. The bag 15.1, which has a capacity of about 20 ml, contains an amount of about 10 ml of a sodium chloride solution. With respect to the connecting lines 3.2 and 3.6, the bag 15.1 is in each case closed by an interruption valve. The bag 15.2, which is connected by the connecting line 3.2 to the bag 15.1 and the mixing bag 11 and is closed by an interruption valve, contains 100 ml of a sodium chloride solution. After the introduction of the umbilical cord blood and/or liquids which permit and/or assist cryopreservation, the connecting lines 3.1 and 3.2 can be hermetically sealed and/or separated by welding. Like the connecting lines 3, the flexible mixing bag 11 substantially consists of a plasticized PVC plastics material, which can be sterilized in a way known, e.g., by autoclaving. The transparent mixing bag 11 is designed for a maximum volume of 180 ml. Arranged on the freezing bag 12, which substantially consists of an EVA plastics material and has two freezing chambers 10, at each freezing container 10 is a removal adaptor 13, which permits the sterile removal of the stored liquid mixture. The connecting lines 3.3 and 3.4 connect the mixing bag 11 and the freezing bag 12 to each other. One of the thin-walled, flexible and transparent connecting lines 3.3 or 3.4 may be a region for storing the mixture of liquids and body fluid. These segments 6, for example five of them, with a capacity of in each case about 1 ml, which are hermetically sealable and separable from one another, not represented in FIG. 8, can be produced by welding from part of the connecting line 3.3 or 3.4.

The two freezing chambers 10 are connected to each other in a communicating manner by a connecting line 3.5. After the hermetic sealing and separating of the connecting lines 3.3, 3.4 and 3.5 from the mixing bag 11 and freezing bag 12, the two freezing chambers 10 are separable from each other.

Figure 9:
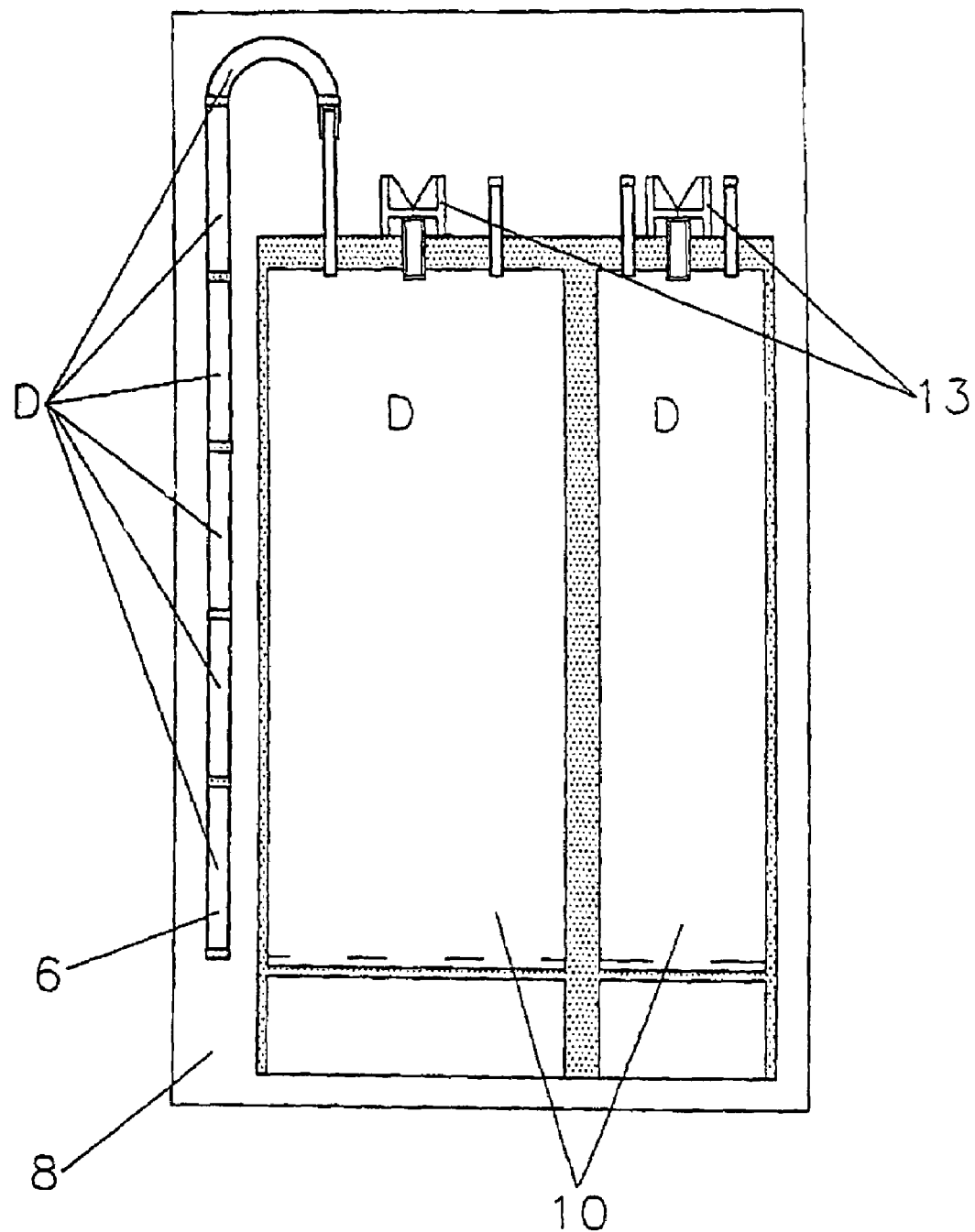

FIG. 9 shows parts of a bag system before freezing. After the separation of the hermetically sealed parts of a bag system which are to be passed on for cryopreservation, that is one or two chambers of the freezing bag 12 or of the mixing and freezing bag 16 and/or the segments 6, which contain a liquid mixture D, comprising umbilical cord blood and liquids which permit and/or assist cryopreservation, the introduction of the aforementioned parts of the bag system into an enclosure 8 takes place. This enclosure 8, which serves in particular for protection from mechanical damage, comprises a cold-resistant plastics film which is sealed in a gas-tight manner by welding.

LIST OF DESIGNATIONS device for the removal of body fluid (1)
shut-off elements (2)
connecting lines (3)
inlet element (4)
outlet element (5)
segments (6)
filling level indication (7)
enclosure (8)
mixing and freezing chamber (9)
freezing chamber (10)
mixing bag (11)
freezing bag (12)
removal adaptor (13)
bag with A (14)
bag with B (15)
mixing and freezing bag (16)
protective bag (17)
glass ampoule (18)
liquid for avoiding blood coagulation (A)
liquid for thinning (B)
cryoprotectant (C)
liquid mixture (D)

We claim:

1. A bag system for collection and cryopreservation of a quantity of body fluid and cells contained therein in a sterile, closed system having a plurality of parts, the system comprising:
    pre-connected device for directly and sterilely collecting body fluid and cells contained therein from a subject's body or blood vessel into the previously sterilized, closed system having a plurality of interconnected sterile parts, separably connected to one another within the closed system, capable of holding or receiving cryopreservation liquids in sterile form without damage to the system, wherein the plurality of parts comprise one or more regions;
    component for holding concentrated cryopreservation liquids in a protected area within the sterile closed system until addition of the cryopreservation liquid to the collected body fluid within the system;
    region for mixing the cryopreservation liquids and a volume of the collected body fluid and cells contained therein to form a mixture, the region having a closable vent for venting air therefrom within the closed system without opening the closed system, wherein the region is airtight when the vent is closed;
    a plurality of shut-off elements and connecting lines, wherein the connecting lines communicatingly connect parts of the bag system to one another within the closed, sterile system, wherein the regions for storing the liquids and the body fluid and mixtures thereof are hermetically sealable and separable from one another without breaching the closed system, and wherein the collected fluids and cells within the sterile, closed bag system are not exposed to outside contamination at any time during collection, processing or cryopreservation.

2. The bag system according to claim 1, wherein the regions for storing the mixture of liquids and the body fluid and cells contained therein comprise at least two chambers of a freezing bag.

3. The bag system according to claim 2, comprising a mixing bag within which is the region for mixing the liquids with the body fluid and cells contained therein, and the freezing bag within which is a region for storing the mixture of liquids and body fluid.

4. The bag system according to claim 3, wherein the freezing bag comprises one freezing chamber.

5. The bag system according to claim 3, wherein the freezing bag comprises at least two freezing chambers.

6. The bag system according to claim 3, comprising a connection between the mixing bag and the freezing bag by two or more connecting lines, at least one of which carries the mixture of liquids and fluids from the mixing bag to the freezing bag or chamber of the freezing bag, and a second line carries air from the mixture of liquids and fluids in the freezing bag or chamber, back to the emptied mixing bag.

7. The bag system according to claim 3, comprising a connection between the mixing bag and the freezing bag by one connecting line.

8. The bag system according to claim 3, configured for cryopreservation of blood, bone marrow, or umbilical cord blood.

9. The bag system according to claim 1, wherein the regions for storing the mixture of liquids and the body fluid and cells contained therein comprise at least two chambers of a mixing/freezing bag.

10. The bag system according to claim 1, wherein one or more regions for storing the mixture of liquids and body fluid and cells contained therein are formed in at least one of the connecting lines having a plurality of hermetically sealable and separable segments.

11. The bag system according to claim 1, further comprising a fill level indicator affixed to the region for mixing the liquids.

12. The bag system according to claim 1, wherein only the regions that are hermetically sealable and separable from one another for storing the mixture of liquids and body fluid and cells contained therein are configured for storing by cryopreservation.

13. The bag system according to claim 1, wherein the parts of the bag system are configured for only single-use.

14. The bag system according to claim 1, wherein the region for mixing the liquids with the body fluid and the region for storing the mixture of liquids and body fluid and cells contained therein comprise a mixing/freezing bag, and wherein the mixing/freezing bag further comprises a mixing/freezing chamber.

15. The bag system according to claim 1, wherein the region for mixing the liquids with the body fluid and the region for storing the mixture of liquids and body fluid and cells contained therein comprise a mixing/freezing bag, and wherein the mixing/freezing bag further comprises a mixing/freezing chamber and a freezing chamber.

16. A method of preparing body fluids and cells contained therein for long-term storage by cryopreservation in a closed, sterile transportation and storage system, the method comprising:
    providing a sterile transportation and storage system having parts pre-connected to one another in a liquid-communicating manner to form a the closed, sterile system;
    introducing body fluid and cells contained therein into the sterile transportation and storage system;
    holding concentrated cryopreservation liquids until needed in a protected area within the closed system where it will not damage the system;
    mixing variable volumes of the body fluid with cryopreservation liquids to form a mixture within the closed system, and venting air therefrom within the closed system as necessary to minimize bubbles while maintaining sterility of the mixture;
    transferring the mixture of cryopreservation liquids and body fluid into a region for storage within the closed transportation and storage system; and
    hermetically sealing and separating the region or the regions for storing the mixture of cryopreservation liquids and body fluid from the remainder of the closed system.

17. The method according to claim 16, further comprising processing body fluids and cells contained therein selected from the group consisting of blood, bone marrow, and umbilical cord blood.

18. The method according to claim 16, wherein the providing step comprises providing the transportation and storage system comprising a bag system for the cryopreservation of a quantity of body fluid and cells contained therein, wherein the system has a plurality of sterilized parts, separably connected to one another within the closed system, and capable of holding or receiving cryopreservation liquids in sterile form, wherein the plurality of parts comprise one or more regions within the closed system, and wherein the system comprises:
    sterile filtration means for directly removing body fluid and cells contained therein from a subject's body or blood vessel;
    a plurality of shut-off elements and connecting lines within the closed system, wherein the connecting lines communicatingly connect parts of the bag system to one another within the closed, sterile system, wherein the regions for storing the liquids and the body fluid and mixtures thereof are hermetically sealable and separable from one another without breaching the closed system.

19. The method according to claim 16, further comprising storing a total amount of liquid in the transportation and storage system in a number of partial amounts, hermetically separated from one another.

20. The method according to claim 16, further comprising carrying out all of the method steps as manual steps.

21. The method according to claim 16, further comprising transferring a defined amount of the mixture of cryopreservation liquids and body fluid into a region for storing.

22. The method of claim 16, further comprising:
venting air from the mixture of liquids and fluids in the storage region via a connecting line; and then
proceeding with the step of sealing and separating the line from the liquid/fluid filled storage region(s), thereby preventing reentry of the air into the storage region(s).

23. The method of claim 22, further comprising:
returning air removed from the mixture of liquids and fluids in the storage region via a connecting line to an emptied region of the system and then
proceeding with the step of sealing and separating the line from the liquid/fluid filled storage region(s), thereby preventing reentry of the air into the storage region(s).

24. The method of claim 16, further comprising:
delivering a portion of the mixture of liquids and body fluids and cells contained therein into a connecting line of the closed system; then
hermetically sealing and separating segments of the line, thereby dividing the mixture contained therein in aliquots $\leq 1$ ml; and then
cryopreserving and storing the segmented line together with, or separately from, the remainder of the liquid/fluid mixture, such that a single segment can be separated and the aliquot independently thawed without disturbing the remainder of the cryopreserved mixture.

* * * * *